United States Patent [19]

Lundbech et al.

[11] Patent Number: 5,696,148

[45] Date of Patent: Dec. 9, 1997

[54] INDOLE COMPOUNDS AND THEIR USE IN TREATING DISEASES OF THE CENTRAL NERVOUS SYSTEM

[75] Inventors: Jane Marie Lundbech, Glostrup; Anders Kanstrup, Virum, both of Denmark

[73] Assignee: Novo Nordisk A/S, Bagsvaerd, Denmark

[21] Appl. No.: 749,520

[22] Filed: Nov. 18, 1996

Related U.S. Application Data

[63] Continuation-in-part of Ser. No. 509,471, Jul. 31, 1995, which is a continuation-in-part of Ser. No. 403,357, Mar. 14, 1995, Pat. No. 5,536,721, and a continuation of PCT/DK96/00332, Jul. 31, 1996 published as WO97/05109, Feb. 13, 1997.

[30] Foreign Application Priority Data

Mar. 14, 1994 [DK] Denmark .................. 0295/94
Jul. 31, 1995 [DK] Denmark .................. 0870/95

[51] Int. Cl.$^6$ .................. A61K 31/40; C07D 209/22; C07D 209/24; C07D 209/30
[52] U.S. Cl. .................. 514/419; 548/312.1; 548/494; 548/505; 514/397; 514/415; 514/419
[58] Field of Search .................. 548/312.1, 494, 548/505; 514/397, 415, 419

[56] References Cited

U.S. PATENT DOCUMENTS

| | | | |
|---|---|---|---|
| 3,931,230 | 1/1976 | Zinnes et al. | 548/505 |
| 4,952,584 | 8/1990 | Thompson et al. | 514/292 |
| 5,122,537 | 6/1992 | Buzzetti et al. | 514/510 |
| 5,284,862 | 2/1994 | Bigge et al. | 514/419 |

FOREIGN PATENT DOCUMENTS

| | | |
|---|---|---|
| 1268772 | 3/1972 | United Kingdom . |
| WO 92/01670 | 2/1992 | WIPO . |

OTHER PUBLICATIONS

Chemical Abstracts, 19525 m JP 72 10390, vol. 77, p. 500 (1972).
Chemical Abstracts, 76325h JP 70 37523, vol. 74, p. 435 (1971).
Blackburn et al., Bioorganic & Medicinal Chemistry Letters, vol. 4, No. 22, pp. 279–284 (1994).
Bolton et al., Biorganic & Medicinal Chemistry Letters, vol. 3, No. 10, pp. 1941–1946 (1993).
Chemical Abstracts, 140005v JP 72 36757, vol. 77, p. 445 (1972).
Kanbe et al., Biosci. Biotech. Biochem., vol. 57, No. 4, pp. 632–635 (1993).

*Primary Examiner*—José G. Dees
*Assistant Examiner*—Laura L. Stockton
*Attorney, Agent, or Firm*—Steve T. Zelson, Esq.; Elias J. Lambiris, Esq.

[57] ABSTRACT

The present invention relates to therapeutically active indole compounds, a method of preparing the same and to pharmaceutical compositions comprising the compounds. The novel compounds are useful in treating diseases in the central nervous system related to the metabotropic glutamate receptor system.

11 Claims, No Drawings

INDOLE COMPOUNDS AND THEIR USE IN TREATING DISEASES OF THE CENTRAL NERVOUS SYSTEM

This application is a continuation-in-part of Ser. No. 08/509,471 filed Jul. 31, 1995 which is a continuation-in-part of Ser. No. 08/403,357 filed Mar. 14, 1995, now U.S. Pat. No. 5,536,721 and a continuation of PCT/DK96/00332 filed Jul. 31, 1996, which are incorporated herein by reference by their entirety.

The present invention relates to therapeutic active indolderivatives, a method for preparing the same, pharmaceutical compositions comprising the compounds and a method of treating diseases in the central nervous system therewith.

Recent molecular biological studies have clearly established the existence of two major types of glutamate receptors in the central nervous system namely the ionotropic and the metabotropic glutamate receptors. The latter is characterised by being G-protein-linked to changes in second messenger formation and modulation of ion channel function, (Meldrum, B. (1991) Epilepsy Res. 10, 55–61, Chapman, A. (1991)in Excitatory Amino Acids p. 265–286, Blackwell scientific publ. ltd., Oxford).

At present 8 different subtypes of the metabotropic glutamate receptors are described (MGluR$_1$ to MGluR$_8$) and in addition some spliced variants of the subtypes are reported.

The Metabotropic glutamate receptor subtypes MGluR$_1$ and MGluR$_5$ are coupled to phosphoinositide hydrolysis (Johnson, G. and Bigge, C. F. (1991) Annu. Rep. Med. Chem. 26, 11–22, Hansen, J. J. and Krogsgaard Larsen, P. Med. Res. Rev. 10, 55–94, Thomsen, C. and Suzdak, P. (1993) Eur. J. Pharmacol. 245, 299), while the others are coupled to cyclic AMP formation (Schoepp, D. D., Johnson, B. G. and Monn, J. A. (1992) J. Neurochem. 58, 1184–1186, Cartmell et al. (1992) J. Neurochem. 58, 1964–1966, Manzoni, O. et al. (1992) Eur. J. Pharmacol. 225, 357–358).

Compounds such as L-glutamate, quisqualate and ibotenate are known to act as non-selective agonists on the metabotropic glutamate receptors, while selective ionotropic glutamate receptor agonists such as NMDA, AMPA and kainate have little effect on these receptors.

Recently a few compounds without activity at the ionotropic glutamate receptors but with activity at the metabotropic receptors have been identified.

These comprise trans-ACPD (trans 1S,3R-1-aminocyclopentane-1,3-dicarboxylic acid), the partial agonist L-AP3 (L-2-amino-3-phosphonopropionic acid) (Palmer, E., Monaghan, D. T. and Cotman, C. W. (1989) Eur. J. Pharmacol. 166, 585–587, Desai, M. A. and Conn, P. J. (1990) Neurosci. Lett. 109, 157–162, Schoepp, D. D. et al. (1991), J. Neurochem. 56, 1789–1796, Schoepp D. D. and Johnson B. G. (1989), J. Neurochem. 53, 1865–1613), L-AP4 (L-2-amino-4-phosphonobutyrate) which is an agonist at the MGluR$_4$ receptor (Thomsen C. et al. (1992), Eur. J. Pharmacol. 227, 361–362) and some of the isomers of CCG (2-(carboxycyclopropyl)glycines) especially L-CCG-I and L-CCG-II (Hayashi, Y. et al. (1992), Br. J. Pharmacol. 107, 539–543).

Very few selective antagonists at the metabotropic glutamate receptors have been reported, however some phenylglycine derivatives S-4CPG (S-4-carboxyphenyl glycine), S-4C3HPG (S-4-carboxy-3-hydroxyphenyl glycine) and S-MCPG (S-alpha methyl-4-carboxyphenyl glycine) have been reported to antagonise trans ACPD stimulated phosphoinositide hydrolysis and thus possibly acting as antagonists at the metabotropic glutamate receptors at the subtypes MGluR$_1$ and MGluR$_5$ (Thomsen, C. and Suzdak, P. (1993) Eur. J. Pharmacol. 245, 299).

Literature evidence suggests that compounds selective for the metabotropic glutamate receptors either as agonists or antagonists are useful in the treatment of different neurological diseases.

The use of compounds active at the metabotropic glutamate receptors for the treatment of epilepsy is corroborated by investigations of the influence of trans-ACPD in the formation of convulsions (Sacaan and Schoepp, (1992), Neurosci. lett. 139, 77) and that phosphoinositide hydrolysis mediated via MGluR is increased after kindling experiments in rats (Akiyama et al. (1992), Brain Res. 569, 71).

Trans-ACPD has been shown to increase release of dopamine in the rat brain which indicates that compounds acting on the metabotropic glutamate receptors might be usable for the treatment of Parkinson's disease and Huntington's Chorea (Sacaan et al. (1992), J. Neurochem. 59, 245).

The use of compounds active at the metabotropic glutamate receptors for treatment of neurological diseases such as senile dementia has been indicated by the findings of Zheng and Gallagher ((1992), Neuron 9, 163) and Bashir et al. ((1993), Nature 363, 347) who demonstrated that activation of metabotropic glutamate receptors are necessary for the induction of long term potentiation (LTP) in nerve cells (septal nucleus, hippocampus) and the finding that long term depression is induced after activation of metabotropic glutamate receptors in cerebellar granule cells (Linden et al. (1991), Neuron 7,81).

Investigations also show that in the treatment of deficiencies of mental and motoric performance seen after conditions of brain ischemia the metabotropic glutamate receptor active compounds may prove usable.

Trans-ACPD has been shown to be a neuroprotective agent in an MCAO model in mice (Chiamulera et al. (1992), Eur. J. Pharmacol. 215, 353), and it has been shown to inhibit NMDA induced neurotoxicity in nerve cell cultures (Koh et al., (1991), Proc. Natl. Acad. Sci. USA 88, 9431).

Also in the treatment of pain the metabotropic glutamate receptor active compounds seem of interest, proved by the fact that antagonists at the metabotropic glutamate receptors antagonises sensory synaptic response to noxious stimuli of thalamic neurons (Eaton, S. A. et al. (1993), Eur. J. Neurosci. 5, 186).

The above findings support that compounds acting on the metabotropic glutamate receptors are useful for the treatment of epilepsy, neurological diseases such as senile dementia, Parkinson's disease, Huntington's Chorea, pain and deficiencies of mental and motoric performance seen after conditions of brain ischemia.

We have now discovered a series of new indolderivatives which are potent antagonists at the metabotropic glutamate receptors.

The present invention relates to compounds of formula Ia

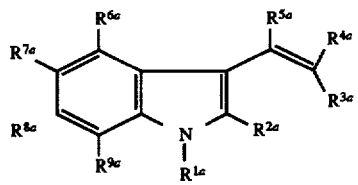

wherein

R$^{1a}$ is C$_{1-6}$-alkyl optionally substituted with halogen; C$_{2-6}$-alkenyl; C$_{2-6}$-alkynyl; C$_{3-6}$-cycloalkyl; C$_{1-6}$-alkyl substituted with $C_{3-6}$-cycloalkyl; carboxy; —$COR^{10a}$; —$COOR^{10a}$; $C_{1-6}$-alkyl substituted with dimethylamino; —$R^{10a}$—O—$R^{11a}$; —$R^{10a}$—O—$R^{11a}$—O—$R^{12a}$; phenylsulfonyl; benzoyl; benzyl; or phenyl; each of which aromatic group is optionally substituted with $C_{1-6}$-alkyl, $C_{1-6}$-alkoxy, halogen, carboxy or nitro; wherein $R^{10a}$, $R^{11a}$ and $R^{12a}$ are independently $C_{1-6}$-alkyl;

$R^{2a}$ is halogen; $C_{1-6}$-alkyl substituted with $C_{3-6}$-cycloalkyl; $C_{3-6}$-cycloalkyl; $C_{2-6}$-alkenyl; $C_{2-6}$-alkynyl; benzyl; $C_{1-6}$-alkyl substituted with dimethylamino; —$R^{10a}$—O—$R^{11a}$; —$R^{10a}$—O—$R^{11a}$—O—$R^{12a}$; wherein $R^{10a}$, $R^{11a}$ and $R^{12a}$ are independently $C_{1-6}$-alkyl; —O optionally substituted with $C_{3-6}$-cycloalkyl, $C_{2-6}$-alkenyl, $C_{2-6}$-alkynyl, phenyl, benzyl, $C_{1-6}$-alkyl substituted with $C_{3-6}$-cycloalkyl or dimethylamino, —$R^{10a}$—O—$R^{11a}$, —$R^{10a}$—O—$R^{11a}$—O—$R^{12a}$, wherein $R^{10a}$, $R^{11a}$ and $R^{12a}$ are independently $C_{1-6}$-alkyl; —S optionally substituted with $C_{1-6}$-alkyl, $C_{3-6}$-cycloalkyl, $C_{2-6}$-alkenyl, $C_{2-6}$-alkynyl, phenyl, benzyl, $C_{1-6}$-alkyl substituted with $C_{3-6}$-cycloalkyl or dimethylamino, —$R^{10a}$—O—$R^{11a}$, —$R^{10a}$—O—$R^{12a}$—O—$R^{12a}$, wherein $R^{10a}$, $R^{11a}$ and $R^{12a}$ are independently $C_{1-6}$-alkyl; —N optionally substituted with one or two $C_{1-6}$-alkyl which alkyl group(s) is/are optionally substituted with hydroxy, morpholino, amino unsubstituted or N-mono or disubstituted with $C_{1-6}$-alkyl, phenyl, phenylsulfonyl or benzyl; morpholino; piperidino; or piperazino optionally N-substituted with $C_{1-6}$-alkyl;

$R^{3a}$ and $R^{4a}$ are independently H; —CN; —$COR^{13a}$; —$COOR^{3a}$; —$SOR^{3a}$; or —$SO_2R^{3a}$; wherein $R^{13a}$ is $C_{1-6}$-alkyl optionally substituted with $C_{3-6}$-cycloalkyl, $C_{3-6}$-cycloalkyl, $C_{2-6}$-alkenyl, $C_{2-6}$-alkynyl, phenyl, benzyl, $C_{1-6}$-alkyl substituted with dimethylamino, —$R^{10a}$—O—$R^{11a}$ or —$R^{10a}$—O—$R^{11a}$—O—$R^{12a}$ wherein $R^{10a}$, $R^{11a}$ and $R^{12a}$ are independently $C_{1-6}$-alkyl; —NH substituted with —$COR^{14a}$ wherein $R^{14a}$ is H or $C_{1-6}$-alkyl; —CONH optionally substituted with H or $C_{1-6}$-alkyl; or 1-methyl-2-imidazolyl; provided that $R^{3a}$ and $R^{4a}$ cannot both be H;

$R^{5a}$ is H or $C_{1-6}$-alkyl; provided that $R^{5a}$ is not H when either $R^{3a}$ or $R^{4a}$ is H;

$R^{6a}$, $R^{7a}$, $R^{8a}$ and $R^{9a}$ are independently H; nitro; amino; halogen; trifluoromethyl; trifluoroacetyl; sulfo; carboxy; carbamoyl; sulfamoyl; —$COR^{10a}$ or —$COOR^{10a}$ wherein $R^{10a}$ is as defined above; $C_{1-6}$-alkoxy; or $C_{1-6}$-alkyl optionally substituted with halogen; or a salt thereof with a pharmaceutically acceptable acid or base.

These salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methanesulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec.butyl, isobutyl, tert.butyl, n-pentyl, 2-methylbutyl, 3-methylbutyl, n-hexyl, 4-methylpentyl, neopentyl, n-hexyl and 2,2-dimethylpropyl.

The term "$C_{1-6}$-alkoxy" as used herein, alone or in combination, refers to a monovalent substituent comprising a lower alkyl group linked through an ether oxygen having its free valence bond from the ether oxygen and having 1 to 6 carbon atoms e.g. methoxy, ethoxy, propoxy, butoxy, pentoxy.

The term "$C_{2-6}$-alkenyl" as used herein refers to an unsaturated hydrocarbon chain having 2–6 carbon atoms and one double bond such as e.g. vinyl, 1-propenyl, allyl, isopropenyl, n-butenyl, n-pentenyl and n-hexenyl.

The term "$C_{3-6}$-cycloalkyl" as used herein refers to a radical of a saturated cyclic hydrocarbon with the indicated number of carbons such as cyclopropyl, cyclobutyl, cyclopentyl, cyclohexyl or cycloheptyl.

The term "$C_{2-6}$-alkynyl" as used herein refers to unsaturated hydrocarbons which contain triple bonds, such as e.g. —C≡CH, —C≡CCH$_3$, —CH$_2$C≡CH, —CH$_2$CH$_2$C≡CH, —CH(CH$_3$)C≡H, and the like.

The term "halogen" means fluorine, chlorine, bromine and iodine.

It is to be understood that the invention extends to both the (E) and the (Z) stereoisomeric forms of the compounds of formula I as well as mixtures of the two.

The preferred compounds of the present invention are those in which $R^{1a}$ is benzyl optionally substituted with $C_{1-6}$-alkyl, $C_{1-6}$-alkoxy, halogen, carboxy or nitro, and/or $R^{3a}$ and $R^{4a}$ are independently —CN; —$COR^{13a}$ or —$COOR^{13a}$; wherein $R^{13a}$ is $C_{1-6}$-alkyl optionally substituted with $C_{3-6}$-cycloalkyl, $C_{3-6}$-cycloalkyl, $C_{2-6}$-alkenyl, $C_{2-6}$-alkynyl, phenyl, benzyl, $C_{1-6}$-alkyl substituted with dimethylamino, —$R^{10a}$—O—$R^{11a}$ or —$R^{10a}$—O—$R^{11a}$—$R^{12a}$ wherein $R^{10a}$, $R^{11a}$ and $R^{12a}$ are independently $C_{1-6}$-alkyl.

The invention also relates to methods of preparing the above mentioned compounds. These methods comprise a) reacting a compound of formula IIa

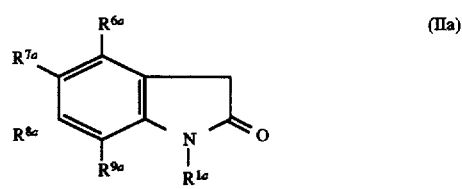

(IIa)

prepared by well known methods, wherein $R^{1a}$, $R^{6a}$, $R^{7a}$, $R^{8a}$, and $R^{9a}$ have the meanings defined above, with a N,N-dimethyl amide, preferably dimethylformamide or dimethylacetamide, and POX$_3$, wherein X is chlorine or bromine, using Vilsmeyer-Hack conditions, to form a compound of formula IIIa

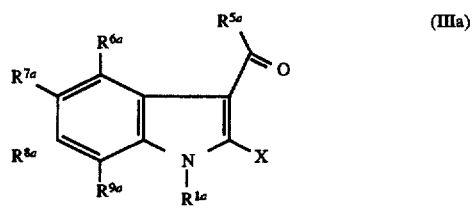

(IIIa)

wherein X is chlorine or bromine, and $R^{1a}$, $R^{5a}$, $R^{6a}$, $R^{7a}$, $R^{8a}$, and $R^{9a}$ have the meanings defined above; and subsequently b) reacting a compound of formula IIIa, wherein X is chlorine or bromine, and $R^{1a}$, $R^{5a}$, $R^{6a}$, $R^{7a}$, $R^{8a}$, and $R^{9a}$ have the meanings defined above, with a compound $R^{14a}$—CH$_2$—$R^{15a}$ wherein $R^{14a}$ and $R^{15a}$ are independently —CN; —$COR^{13a}$; —$COOR^{13a}$; —$SOR^{13a}$; or —$SO_2R^{13a}$; wherein $R^{13a}$ have the meanings defined above, either in the presence or absence of an added base, preferable triethylamine, piperidine or potassium carbonate, to form a compound of formula IVa,

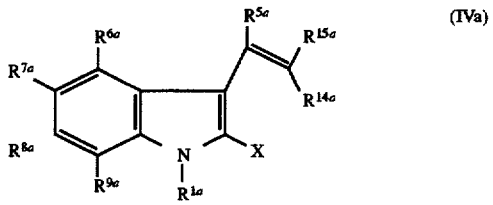
(IVa)

wherein $R^{1a}$, $R^{5a}$, $R^{6a}$, $R^{7a}$, $R^{8a}$, $R^{9a}$, $R^{14a}$ and $R^{15a}$ have the meanings defined above, or c) reacting a compound of formula Va, (Va)

prepared by well known methods, wherein $R^{1a}$, $R^{6a}$, $R^{7a}$, $R^{8a}$, and $R^{9a}$ have the meanings defined above and $R^{16a}$ is $C_{1-6}$-alkyl optionally substituted with $C_{3-6}$-cycloalklyl; $C_{3-6}$-cycloalkyl; $C_{2-6}$-alkenyl; $C_{2-6}$-alkynyl; phenyl; benzyl; $C_{1-6}$-alkyl substituted with dimethylamino; $R^{10a}$—O—$R^{11a}$; —$R^{10a}$—O—$R^{11a}$—O—$R^{12a}$; wherein $R^{10a}$, $R^{11a}$ and $R^{12a}$ are independently $C_{1-6}$-alkyl; with a N,N-dimethyl amide, preferably dimethylformamide or dimethylacetamide, and $POX_3$, wherein X is chlorine or bromine, using Vilsmeyer-Hack conditions, to form a compound of formula VIa, (VIa)

wherein $R^{1a}$, $R^{5a}$, $R^{6a}$, $R^{7a}$, $R^{8a}$, $R^{9a}$ and $R^{16a}$ have the meanings defined above, and subsequently d) reacting a compound of formula VIa wherein $R^{1a}$, $R^{5a}$, $R^{6a}$, $R^{7a}$, $R^{8a}$, $R^{9a}$ and $R^{16a}$ have the meanings defined above, with a compound $R^{14a}$—$CH_2$—$R^{15a}$ wherein $R^{14a}$ and $R^{15a}$ are independently —CN; —$COR^{13a}$; —$COOR^{13a}$; —$SOR^{13a}$; or —$SO_2R^{13a}$; wherein $R^{13a}$ have the meanings defined above, either in the presence or absence of an added base, preferable triethylamine, piperidine or potassium carbonate to form a compound of formula VIIa, (VIIa)

wherein $R^{1a}$, $R^{5a}$, $R^{6a}$, $R^{7a}$, $R^{8a}$, $R^{9a}$, $R^{14a}$, $R^{15a}$ and $R^{16a}$ have the meanings defined above, or e) reacting a compound of formula VIa, wherein $R^{1a}$, $R^{5a}$, $R^{6a}$, $R^{7a}$, $R^{8a}$, $R^{9a}$ and $R^{16a}$ have the meanings defined above, with a compound $R^{14a}$—$CH_2$—$PO(R^{17a})_2$, wherein $R^{3a}$ have the meaning defined above, and $R^{17a}$ is —O-alkyl, under Wittig or Horner-Emmons conditions, to form a compound of formula VIIIa, (VIIIa)

wherein $R^{1a}$, $R^{5a}$, $R^{6a}$, $R^{7a}$, $R^{8a}$, $R^{9a}$, $R^{14a}$ and $R^{16a}$ have the meanings defined above, or f) reacting a compound of formula VIa, wherein $R^{1a}$, $R^{5a}$, $R^{6a}$, $R^{7a}$, $R^{8a}$, $R^{9a}$ and $R^{16a}$ have the meanings defined above, with a compound $R^{14a}$—$CH(R^{4a})$—$PO(R^{17a})_2$, wherein $R^{14a}$ have the meanings defined above and $R^{17a}$ is —O-alkyl, under Wittig or Horner-Emmons conditions, to form a compound of formula IXa, (IXa)

wherein $R^{1a}$, $R^{4a}$, $R^{5a}$, $R^{6a}$, $R^{7a}$, $R^{8a}$, $R^{9a}$, $R^{14a}$, and $R^{16a}$ have the meanings defined above, or g) reacting a compound of formula IIIa, wherein X is chlorine or bromine, and $R^{1a}$, $R^{5a}$, $R^{6a}$, $R^{7a}$, $R^{8a}$, and $R^{9a}$ have the meanings defined above, with an alkali metal salt of a compound HO-$R^{18a}$ or HS-$R^{18a}$, prepared previously or in situ, wherein $R^{18a}$ is $C_{1-6}$-alkyl optionally substituted with $C_{3-6}$-cycloalkyl, $C_{3-6}$-cycloalkyl, $C_{2-6}$-alkenyl, $C_{2-6}$-alkynyl, phenyl, benzyl, $C_{1-6}$-alkyl substituted with dimethylamino, $R^{10a}$—O—$R^{11a}$, —$R^{10a}$—O—$R^{11a}$—O—$R^{12a}$; wherein $R^{10a}$, $R^{11a}$ and $R^{12a}$ are independently $C_{1-6}$-alkyl, to form a compound of formula Xa, (Xa)

wherein $Y^a$ is —O— or —S—, and $R^{1a}$, $R^{5a}$, $R^{6a}$, $R^{7a}$, $R^{8a}$, $R^{9a}$, and $R^{18a}$ have the meanings defined above, and subsequently h) reacting a compound of formula Xa, wherein $Y^a$ is —O— or —S—, and $R^{1a}$, $R^{5a}$, $R^{6a}$, $R^{7a}$, $R^{8a}$, $R^{9a}$, and $R^{18a}$ have the meanings defined above, under the conditions defined in paragraphs b, d, e, or f, to give a compound of formula XIa,

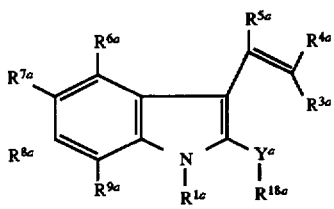

(XIa)

wherein $Y^a$, $R^{1a}$, $R^{3a}$, $R^{4a}$, $R^{5a}$, $R^{6a}$, $R^{7a}$, $R^{8a}$, $R^{9a}$, and $R^{18a}$ have the meanings defined above, or i) reacting a compound of formula formula VIa, wherein $R^{1a}$, $R^{5a}$, and $R^{16a}$ have the meanings defined above, and at least one of $R^{6a}$, $R^{7a}$, $R^{8a}$, or $R^{9a}$ is H with well known reactive substrates leading to aromatic substitution using the reaction conditions known in the art, to form a compound of formula VIa, wherein $R^{6a}$, $R^{7a}$, $R^{8a}$, or $R^{9a}$ have the meanings defined above provided that at least one of $R^{6a}$, $R^{7a}$, $R^{8a}$, or $R^{9a}$ is not H.

Specific examples of the compounds of formula Ia are the following:

Ethyl 2-cyano-3-(1-benzyl-2-chloro-3-indolyl)acrylate,
Ethyl 2-cyano-3-(1-methyl-2-chloro-3-indolyl)acrylate,
3-(1-Methyl-2-chloro-3-indolyl)-2-methylsulfonyl-acrylonitrile,
3-(1-Benzyl-2-chloro-3-indolyl)-2-methylsulfonylacrylonitrile,
3-(1-Cyclopropylmethyl-2-chloro-3-indolyl)-2-(1-methyl-2-imidazolylsulfonyl) acrylonitrile,
3-(1-Methyl-2-chloro-3-indolyl)-2-(2-propylsulfonyl) acrylonitrile,
3-(1-Benzyl-2-methylthio-3-indolyl)-2-methylsulfonyl acrylonitril,
Ethyl 2-cyano-3-(1-(4-chlorobenzyl)-2-chloro-3-indolyl) acrylate,
Ethyl 2-cyano-3-(1-(3-chlorobenzyl)-2-chloro-3-indolyl) acrylate,
Ethyl 2-cyano-3-(1-(2-chlorobenzyl)-2-chloro-3-indolyl) acrylate,
Ethyl 2-cyano-3-(1-(4-methoxybenzyl)-2-chloro-3-indolyl) acrylate,
Ethyl 2-cyano-3-(1-(3-methoxybenzyl)-2-chloro-3-indolyl) acrylate,
Ethyl 2-cyano-3-(1-(2-methoxybenzyl)-2-chloro-3-indolyl) acrylate,
Ethyl 2-ethoxycarbonyl-3-(1-(4-chlorobenzyl)-2-chloro-3-indolyl)acrylate,
Ethyl 2-ethoxycarbonyl-3-(1-(4-methoxybenzyl)-2-chloro-3-indolyl)acrylate,
Ethyl 2-cyano-3-(1-benzyl-2-chloro-3-indolyl)acrylonitrile,
Ethyl 2-cyano-3-(1-(4-methoxybenzyl)-2-chloro-3-indolyl) acrylonitrile,
Ethyl 2-cyano-3-(1-(4-chlorobenzyl)-2-chloro-3-indolyl) acrylonitrile
Ethyl 2-cyano-3-(1-methyl-2-chloro-3-indolyl)acrylonitrile,
Methyl 3-(1-benzyl-2-chloro-3-indolyl)-2-methoxycarbonylacrylate,
Methyl 3-(1-(4-methoxybenzyl)-2-chloro-3-indolyl)-2-methoxycarbonylacrylate,
Methyl 3-(1-(4-chlorobenzyl)-2-chloro-3-indolyl)-2-methoxycarbonylacrylate,
Methyl 3-(1-methyl-2-chloro-3-indolyl)-2-methoxycarbonylacrylate,
3-(1-benzyl-2-chloro-3-indolyl)-2-ethoxycarbonylacrylamide,
3-(1-(4-methoxybenzyl)-2-chloro-3-indolyl)-2-ethoxycarbonylacrylamide,
3-(1-(4-chlorobenzyl)-2-chloro-3-indolyl)-2-ethoxycarbonylacrylamide,
2-Ethoxycarbonyl-3-(1-methyl-2-chloro-3-indolyl) acrylamide,
2-Ethoxycarbonyl-3-(1-benzyl-2-chloro-3-indolyl)-N-methylacrylamide,
2-Ethoxycarbonyl-3-(1-(4-methoxybenzyl)-2-chloro-3-indolyl)-N-methylacrylamide,
2-Ethoxycarbonyl-3-(1-(4-chlorobenzyl)-2-chloro-3-indolyl)-N-methylacrylamide,
2-Ethoxycarbonyl-3-(1-methyl-2-chloro-3-indolyl)-N-methylacrylamide.

The pharmacological properties of the compounds of the invention can be illustrated by determining their effects in different conventional radioligand binding assays or in functional in vitro assays.

The compounds of the invention were studied in an in vitro assay for measuring inhibition of PI-hydrolysis in BHK 570 cells expressing $mGluR_1\alpha$ receptors.

Principle

The metabotropic glutamate receptor (mGluR) is selectively activated by trans-aminocyclopentane dicarboxylic acid and is coupled to the hydrolysis of inositol phosphates via a GTP-binding protein. At the molecular level, cDNAs encoding eight subtypes of the mGluR family have been isolated. The first subtype isolated (Houamed et al., 1991, Science 252, 1318), termed the mGluR1α, has been shown to be coupled to PI-hydrolysis when expressed in baby hamster kidney cells (BHK) (Thomsen et al., Brain Res. (in press)). In these cells no stimulation by 1 mM quisqualate or glutamate was observed with control BHK cells whereas a 6–8 fold increase over basal PI-hydrolysis was seen with BHK cells expressing mGluR1α.

Cell Culture

BHK570 cells expressing mGluR1α are cultured in DMEM (4.5 g/l glucose, 2 mM glutamin); 5% foetal calf serum; 0.10 mg/ml neomycin; 0.5 mg/ml G418; 1 µM methotrexate; 50 µg/ml gentamycin. Cells are subcultured every 5 days using 0.05% trypsin/EDTA in PBS.

Inositol Phosphate Formation

The protocol for PI-hydrolysis was measured using a modification of a method previously described (Berridge et al., 1982, Biochem. J. 206,587). Cells were plated in 16 mm wells (24 well multidish, Costar) with 1 confluent 100 mm dish per multidish. Replace the medium 24 h before the experiment with 500 µl fresh growth medium containing 4 µCi/ml myo-[2-³H]inositol (specific activity 18 Ci/mmol, Amersham). The cells were washed twice with Krebs-Henseleit buffer (Sigma cat. #3753: glucose 2.0 g/l, $MgSO_4$ 0.141 g/l, $KHPO_4$ 0.16 g/l, KCl 0.35 g/l, NaCl 6.90 g/l and $NaHCO_3$ 2.1 g/l) supplemented with 10 mM LiCl and 2.5 mM $CaCl_2$. The buffer was equilibrated with 5% $CO_2$, 95% air to pH 7.5 at 37° C. Following 5 min of preincubation in the above buffer, buffer or test compounds were added and cells were incubated for 30 min at 37° C. In antagonist studies, add test compounds 5 min prior to agonist stimulation. R-formation was stopped by placing the cells on ice and quickly aspirating the media. The wells were washed once with ice-cold Krebs-Henseleit buffer and subsequently 1 ml ice-cold 10% perchloric acid was added to each well. Place the cells on ice for 20 min. In Nunc minisorp test tubes (75×12 mm, cat. #443990): add 250 µl of 10 mM EDTA, pH 7.0+5% Universal Indicator (Merck). Transfer the PCA extract to each tube containing the pH-indicator. Neutralize the samples with 1.5M KOH+60 mM HEPES to pH 7.5 (~1100–1200 µl). Centrifugate (6.000 rpm, 5 min, 0° C.). They can be stored frozen at this point. Fractions of inositolphosphates were separated using ion-exchange columns (Amersham, RPN 1908) according to the method provided by Amersham.

Separation of Inositol Phosphates on Ion-Exchange Columns

Prepare columns with 5 ml 1M KHCO$_3$ and wash with 15 ml dist. water. Adjust vacuum so that the flow-rate does not exceed 5 ml/min. Add 4 ml dist. water and subsequently 1 ml [$^3$H]InsP sample. Wash with 5 ml dist. water. IP1 to IP4 fractions may be collected with 5 ml 0.05; 0.10; 0.17 and 0.25M KHCO$_3$, respectively. Usually IP1 and IP2 fractions are collected simultaneously. Scintillation liquid: use 12–15 ml Ultima Gold (Packard).

Testprocedure

Testcompounds are dissolved in DMSO, DMSO and Pluronic F-127 or ethanol and diluted in assay buffer. Glutamate (10 µM and 1000 µM) and buffer alone are included as a control.

Results

The stimulation by 10 µM shall represent a submaximal stimulation. The response by 10 µM glutamate should exceed 3-fold the basal level and should be below maximal stimulation (glutamate at 1 mM). The results are calculated relative to the stimulation by 10 µM glutamate and a dose response curve is generated.

Examples of test results obtained by testing a compound of the present invention in the above mentioned assay appear from the following Table 1.

TABLE 1

| Compound No. | IC$_{50}$ (µM) |
|---|---|
| 1 | 2.2 |

The compounds according to the invention are effective over a wide dosage range. For example, in the treatment of adult humans, dosages from about 0.05 to about 100 mg, preferably from about 0.1 to about 100 mg, per day may be used. A most preferable dosage is about 10 mg to about 70 mg per day. In choosing a regimen for patients suffering from a disease in the central nervous system related to the metabotropic glutamate receptor system it may frequently be necessary to begin with a dosage of from about 30 to about 70 mg per day and when the condition is under control to reduce the dosage as low as from about 1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

Typical compositions include a compound of formula I or a pharmaceutically acceptable acid addition salt thereof, associated with a pharmaceutically acceptable carrier. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| | |
|---|---|
| Active compound | 5.0 mg |
| Lactosum | 67.8 mg Ph. Eur. |
| Avicel ® | 31.4 mg |
| Amberlite ® | 1.0 mg |
| *Magnesii stearas* | 0.25 mg Ph. Eur. |

The invention will now be described in further detail with reference to the following examples.

EXAMPLE 1a

Ethyl 2-cyano-3-(1-benzyl-2-chloro-3-indolyl) acrylate (1a)

To 5.83 g of 1-benzyl-2-chloroindole-3-carbaldehyde, dissolved in 200 ml of abs. EtOH, was added 6.1 g of ethyl 2-cyanoacetate and 6.6 g of triethylamine. After 4 days with stirring, the solution was added to water, and the precipitate collected by filtration and dried to give (1a). Yield 6.72 g of (1a), m.p. 130°–131° C.

EXAMPLE 2a

Ethyl 2-cyano-3-(1-methyl-2-chloro-3-indolyl) acrylate (2a)

To 2 g of 1-methyl-2-chloroindole-3-carbaldehyde, dissolved in 50 ml of abs. EtOH, was added 2.3 g of ethyl 2-cyanoacetate and 4.2 g of triethylamine. After 19 hours with stirring, the solution was added to 200 ml of water, and the precipitate collected by filtration and dried to give (2a). Yield 2.68 g of (2a), m.p. 131°–132° C.

EXAMPLE 3a 3-(1-Methyl-2-chloro-3-indolyl)-2-methylsulfonylacrylonitrile (3a)

To 550 mg of 1-methyl-2-chloroindole-3-carbaldehyde, dissolved in 25 ml of THF, was added 730 mg of methylsulfonylacetonitril and 1.2 g of triethylamine. After 24 hours another 300 mg of methylsulfonylacetonitril was added, and the mixture was stirred for 6 days. The precipitate was collected by filtration to give (3a). Yield 630 mg of (3a), m.p. 180° C.

EXAMPLE 4a 3-(1-Benzyl-2-chloro-3-indolyl)-2-methylsulfonylacrylonitrile (4a)

To 1 g of 1-benzyl-2-chloroindole-3-carbaldehyde, dissolved in 25 ml of THF, was added 930 mg of methylsulfonylacetonitril and 1.6 g of triethylamine. After 24 hours another 1 g of methylsulfonylacetonitril and 0.3 g of triethylamine was added, and the mixture was stirred for 6 days. The precipitate was collected by filtration to give (4a). Yield 1.1 g of (4a), m.p. 206° C.

EXAMPLE 5a 3-(1-Cyclopropylmethyl-2-chloro-3-indolyl)-2-(1-methyl-2-imidazolylsulfonyl)acrylonitrile (5a)

To 1 g of 1-cyclopropylmethyl-2-chloroindole-3-carbaldehyde, dissolved in 50 ml of MeOH, was added 880 mg of 1-methylimidazol-2-ylsulfonylacetonitril and 1.6 ml of triethylamine. The mixture was stirred for 24 hours. The precipitate was collected by filtration to give (5a). Yield 1.45 g of (5a), m.p. 214° C.

EXAMPLE 6a 3-(1-Methyl-2-chloro-3-indolyl)-2-(2-propylsulfonyl)acrylonitrile (6a)

To 1 g of 1-methyl-2-chloroindole-3-carbaldehyde, dissolved in 25 ml of MeOH, was added 820 mg of propan-2-propylsulfonylacetonitril and 1.6 ml of triethylamine. After 24 hours another 300 mg of methylsulfonylacetonitril was added, and the mixture was stirred for 48 hours. The precipitate was collected by filtration to give (6a). Yield 1.13 g of (6a), m.p. 141C.

EXAMPLE 7a

1-Benzyl-2-methylthioindole-3-carbaldehyde (7a)

To 5 g of 1-benzyl-2-chloroindole-3-carbaldehyde, dissolved in MeOH, was added 2.5 g of sodium methylmercaptan, and the mixture was stirred overnight. The precipitate was collected by filtration, washed with MeOH and water to give (7a). Yield 5.15 g of (7a).

EXAMPLE 8a 3-(1-Benzyl-2-methylthio-3-indolyl)-2-methylsulfonylacrylonitril (8a)

To 1 g of (7a), dissolved in 50 ml of MeOH, was added 850 mg of methylsulfonylacetonitril and 1.5 ml triethylamine. After 24 hours of stirring another 300 mg of methylsulfonylacetonitril was added. After further 24 hours with stirring the precipitate was collected by filtration, washed with MeOH and water, to give (8a). Yield 990 mg of (8a), m.p. 125°–126° C.

EXAMPLE 9a

Ethyl 2-cyano-3-(1-(4-chlorobenzyl)-2-chloro-3-indolyl)acrylate (9a)

To 608 mg of 1-(4-chlorobenzyl)-2-chloroindolecarbaldehyde, slurried in 10 ml of ethanol, was added 608 mg of potassium carbonate and 0.24 ml of ethyl cyanoacetate. After overnight stirring 10 ml of water was added, and the product collected by filtration, washed with water, and dried to give (9a). Yield 650 mg of (9a). M.p. 179°–80° C. (sample recryst. from EtOH).

EXAMPLE 10a

Ethyl 2-cyano-3-(1-(3-chlorobenzyl)-2-chloro-3-indolyl)acrylate (10a)

To 500 mg of 1-(3-chlorobenzyl)-2-chloroindolecarbaldehyde, slurried in 10 ml of ethanol, was added 500 mg of potassium carbonate and 0.19 ml of ethyl cyanoacetate. After overnight stirring 10 ml of water was added, and the product collected by filtration, washed with water, and dried to give (10a). Yield 510 mg of (10a). M.p. 130.5°–132° C. (sample recryst. from EtOH).

EXAMPLE 11a

Ethyl 2-cyano-3-(1-(2-chlorobenzyl)-2-chloro-3-indolyl)acrylate (11a)

To 608 mg of 1-(2-chlorobenzyl)-2-chloroindolecarbaldehyde, slurried in 10 ml of ethanol, was added 608 mg of potassium carbonate and 0.24 ml of ethyl cyanoacetate. After overnight stirring 10 ml of water was added, and the product collected by filtration, washed with water, and dried to give (10a). Yield 590 mg of (11a). M.p. 139.5°–140.5° C. (sample recryst. from EtOH).

EXAMPLE 12a

Ethyl 2-cyano-3-(1-(4-methoxybenzyl)-2-chloro-3-indolyl)acrylate (12a)

To 600 mg of 1-(4-methoxybenzyl)-2-chloroindolecarbaldehyde, slurried in 10 ml of ethanol, was added 608 mg of potassium carbonate and 0.24 ml of ethyl cyanoacetate. After overnight stirring 10 ml of water was added, and the product collected by filtration, washed with water, and dried to give (12a). Yield 620 mg of (12a). M.p. 153°–4° C. (sample recryst. from EtOH).

EXAMPLE 13a

Ethyl 2-cyano-3-(1-(2-methoxybenzyl)-2-chloro-3-indolyl)acrylate (13a)

To 600 mg of 1-(2-methoxybenzyl)-2-chloroindolecarbaldehyde, slurried in 10 ml of ethanol, was added 608 mg of potassium carbonate and 0.24 ml of ethyl cyanoacetate. After overnight stirring 10 ml of water was added, and the product collected by filtration, washed with water, and dried to give (12a). Yield 630 mg of (12a). M.p. 126°–8° C. (sample recryst. from EtOH/water).

EXAMPLE 14a

Ethyl 2-ethoxycarbonyl-3-(1-(4-chlorobenzyl)-2-chloro-3-indolyl)acrylate (14a)

To 500 mg of 1-(4-Chlorobenzyl)-2-chloroindolecarbaldehyde, dissolved in 15 ml of a solvent which consisted of 5% piperidine and 2% acetic acid in absolute ethanol, was added 0.28 ml of diethyl malonate. After stirring for 3 days the solvent was removed by evaporation, and the product dissolved in 25 ml of ether plus 25 ml of 1N HCl. The organic phase was separated, and washed with 25 ml 1N HCl, 25 ml water, 25 ml of saturated NaHCO3 solution, dried (MgSO4) and evaporated to give an oil. Purification by column chromatography (methylene chloride on silica 60) gave (14a) as an oil which slowly crystallized. Yield 210 mg. M.p. 98°–99° C. (sample recryst. from EtOH/water).

EXAMPLE 15a

Ethyl 2-ethoxycarbonyl-3-(1-(4-methoxybenzyl)-2-chloro-3-indolyl)acrylate (15a)

To 460 mg of 1-(4-methoxybenzyl)-2-chloroindolecarbaldehyde, dissolved in 15 ml of a solvent which consisted of 5% piperidine and 2% acetic acid in absolute ethanol, was added 0.26 ml of diethyl malonate. After stirring for 3 days the solvent was removed by evaporation, and the product dissolved in 25 ml of ether plus 25 ml of 1N HCl. The organic phase was separated, and washed with 25 ml 1 N HCl, 25 ml water, 25 ml of saturated NaHCO3 solution, dried (MgSO4) and evaporated to give an oil. Purification by column chromatography (methylene chloride on silica 60) gave (15a) as an oil. 1H-NMR (CDCl3): 8.03 (s, 1H); 7.50 (m, 1H); 7.20 (m, 3H); 7.02 (d, 2H); 6.78 (d, 2H); 5.30 (s, 2H); 4.32 (q, 2H); 4.24 (q, 2H); 3.71 (s, 3H); 1.33 (t, 3H) 1.11 (t, 3H).

We claim:

1. A compound of formula Ia

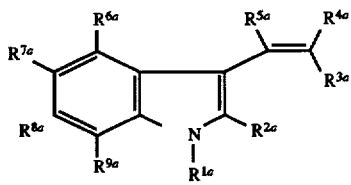

wherein $R^{1a}$ is $C_{1-6}$-alkyl optionally substituted with halogen; $C_{2-6}$-alkenyl; $C_{2-6}$-alkynyl; $C_{3-6}$-cycloalkyl; $C_{1-6}$-alkyl substituted with $C_{3-6}$-cycloalkyl; carboxy; —$COR^{10a}$; —$COOR^{10a}$; $C_{1-6}$-alkyl substituted with dimethylamino; —$R^{10a}$—O—$R^{11a}$; —$R^{10a}$—O—$R^{11a}$—O—$R^{12a}$; phenylsulfonyl benzoyl; benzyl; or phenyl; each of which aromatic groups is optionally substituted with $C_{1-6}$-alkyl, $C_{1-6}$-alkoxy, halogen, carboxy or nitro; wherein $R^{10a}$, $R^{11a}$, and $R^{12a}$ are independently $C_{1-6}$-alkyl;

$R^{2a}$ is halogen; $C_{1-6}$-alkyl substituted with $C_{3-6}$-cycloalkyl; $C_{3-6}$-cycloalkyl; $C_{2-6}$-alkenyl; $C_{2-6}$-alkynyl; benzyl; $C_{1-6}$-alkyl substituted with dimethylamino; —$R^{10a}$—O—$R^{11a}$; —$R^{10a}$—O—$R^{11a}$—O—$R^{12a}$; wherein $R^{10a}$, $R^{11a}$ and $R^{12a}$ are independently $C_{1-6}$-alkyl; —O substituted with $C_{3-6}$-cycloalkyl, $C_{2-6}$-alkenyl, $C_{2-6}$-alkynyl, phenyl, benzyl, $C_{1-6}$-alkyl substituted with $C_{3-6}$-cycloalkyl or dimethylamino, —$R^{10a}$—O—$R^{11a}$, —$R^{10a}$—O—$R^{11a}$—O—$R^{12a}$, wherein $R^{10a}$, $R^{11a}$ and $R^{12a}$ are independently $C_{1-6}$-alkyl; —S substituted with $C_{1-6}$alkyl, $C_{3-6}$-cycloalkyl, $C_{2-6}$-alkenyl, $C_{2-6}$-alkynyl, phenyl, benzyl, $C_{1-6}$-alkyl substituted with $C_{3-6}$-cycloalkyl or dimethylamino, —$R^{10a}$—O—$R^{11a}$, —$R^{10a}$—O—$R^{11a}$—O—$R^{12a}$, wherein $R^{10a}$, $R^{11a}$ and $R^{12a}$ are independently $C_{1-6}$-alkyl; —N substituted with one or two $C_{1-6}$-alkyl which alkyl group(s) is/are optionally substituted with hydroxy, morpholino, amino unsubstituted or N-mono or disubstituted with $C_{1-6}$-alkyl, phenyl, phenylsulfonyl or benzyl; morpholino; piperidino; or piperazino optionally N-substituted with $C_{1-6}$-alkyl;

$R^{3a}$ and $R^{4a}$ are independently H; —CN; —$COR^{13a}$; —$COOR^{13a}$; —$SOR^{13a}$; or —$SO_2R^{13a}$; wherein $R^{13a}$ is $C_{1-6}$-alkyl optionally substituted with $C_{3-6}$-cycloalkyl, $C_{3-6}$-cycloalkyl, $C_{2-6}$-alkenyl, $C_{2-6}$-alkynyl, phenyl, benzyl, $C_{1-6}$-alkyl substituted with dimethylamino, —$R^{10a}$—O—$R^{11a}$ or —$R^{10a}$—O—$R^{11a}$—O—$R^{12a}$ wherein $R^{10a}$, $R^{11a}$ and $R^{12a}$ are independently $C_{1-6}$-alkyl; —NH substituted with —$COR^{14a}$ wherein $R^{14a}$ is H or $C_{1-6}$-alkyl; —CONH optionally substituted with H or $C_{1-6}$-alkyl; or 1-methyl-2-imidazolyl; provided that $R^{3a}$ and $R^{4a}$ cannot both be H;

$R^{5a}$ is H or $C_{1-6}$-alkyl; provided that $R^{5a}$ is not H when either $R^{3a}$ or $R^{4a}$ is H; and $R^{6a}$, $R^{7a}$, $R^{8a}$ and $R^{9a}$ are independently H; nitro; amino; halogen; trifluoromethyl; trifluoroacetyl; sulfo; carboxy; carbamoyl; sulfamoyl; —$COR^{10a}$ or —$COOR^{10a}$ wherein $R^{10a}$ is as defined above; $C_{1-6}$-alkoxy; or $C_{1-6}$-alkyl optionally substituted with halogen; or a salt thereof with a pharmaceutically acceptable acid or base.

2. A compound according to claim 1 wherein $R^{1a}$ is benzyl optionally substituted with $C_{1-6}$-alkyl, $C_{1-6}$-alkoxy, halogen, carboxy or nitro.

3. A compound according to claim 1 wherein $R^{3a}$ and $R^{4a}$ are independently —CN; —$COR^{13a}$ or —$COOR^{13a}$; wherein $R^{13a}$ is $C_{1-6}$-alkyl optionally substituted with $C_{3-6}$-cycloalkyl, $C_{3-6}$-cycloalkyl, $C_{2-6}$-alkenyl, $C_{2-6}$-alkynyl, phenyl, benzyl, $C_{1-6}$-alkyl substituted with dimethylamino, —$R^{10a}$—O—$R^{11a}$ or —$R^{10a}$—O—$R^{11a}$—O—$R^{12a}$ wherein $R^{10a}$, $R^{11a}$ and $R^{12a}$ are independently $C_{1-6}$-alkyl.

4. A compound according to claim 1 which is

Ethyl 2-cyano-3-(1-(4-chlorobenzyl)-2-chloro-3-indolyl)acrylate,

Ethyl 2-cyano-3-(1-(3-chlorobenzyl)-2-chloro-3-indolyl)acrylate,

Ethyl 2-cyano-3-(1-(2-chlorobenzyl)-2-chloro-3-indolyl)acrylate,

Ethyl 2-cyano-3-(1-(4-methoxybenzyl)-2-chloro-3-indolyl)acrylate,

Ethyl 2-cyano-3-(1-(3-methoxybenzyl)-2-chloro-3-indolyl)acrylate,

Ethyl 2-cyano-3-(1-(2-methoxybenzyl)-2-chloro-3-indolyl)acrylate,

Ethyl 2-ethoxycarbonyl-3-(1-(4-chlorobenzyl)-2-chloro-3-indolyl)acrylate,

Ethyl 2-ethoxycarbonyl-3-(1-(4-methoxybenzyl)-2-chloro-3-indolyl)acrylate,

Ethyl 2-cyano-3-(1-benzyl-2-chloro-3-indolyl)acrylonitrile,

Ethyl 2-cyano-3-(1-(4-methoxybenzyl)-2-chloro-3-indolyl)acrylonitrile,

Ethyl 2-cyano-3-(1-(4-chlorobenzyl)-2-chloro-3-indolyl)acrylonitrile,

Ethyl 2-cyano-3-(1-methyl-2-chloro-3-indolyl)acrylonitrile,

Methyl 3-(1-benzyl-2-chloro-3-indolyl)-2-methoxycarbonylacrylate,
Methyl 3-(1-(4-methoxybenzyl)-2-chloro-3-indolyl)-2-methoxycarbonylacrylate,
Methyl 3-(1-(4-chlorobenzyl)-2-chloro-3-indolyl)-2-methoxycarbonylacrylate,
Methyl 3-(1-methyl-2-chloro-3-indolyl)-2-methoxycarbonylacrylate,
3-(1-benzyl-2-chloro-3-indolyl)-2-ethoxycarbonylacrylamide,
3-(1-(4-methoxybenzyl)-2-chloro-3-indolyl)-2-methoxycarbonylacrylamide,
3-(1-(4-chlorobenzyl)-2-chloro-3-indolyl)-2-ethoxycarbonylacrylamide,
2-Ethoxycarbonyl-3-(1-methyl-2-chloro-3-indolyl) acrylamide,
2-Ethoxycarbonyl-3-(1-benzyl-2-chloro-3-indolyl)-n-methylacrylamide,
2-Ethoxycarbonyl-3-(1-(4-methoxybenzyl)-2-chloro-3-indolyl)-N-methylacrylamide,
2-Ethoxycarbonyl-3-(1-(4-chlorobenzyl)-2-chloro-3-indolyl)-N-methylacrylamide,
2-Ethoxycarbonyl-3-(1-methyl-2-chloro-3-indolyl)-N-methylacrylamide, or a pharmaceutically acceptable salt thereof.

5. A compound according to claim 1 which is

Ethyl 2-cyano-3-(1-methyl-2-chloro-3-indolyl)acrylate,
3(1-Methyl-2-chloro-3-indolyl)-2-methylsulfonylacrylonitrile,
3-(1-Benzyl-2-chloro-3-indolyl)-2-methylsulfonylacrylonitrile,
3-(1-Cyclopropylmethyl-2-chloro-3-indolyl)-2-(1-methyl-2-imidazolylsulfonyl) acrylonitrile,
3-(1-Methyl-2-chloro-3-indolyl)-2-(2-propylsulfonyl) acrylonitrile,
3-(1-Benzyl-2-methylthio-3-indolyl)-2-methylsulfonylacrylonitrile, or a pharmaceutically acceptable salt thereof.

6. A compound according to claim 1 which is Ethyl 2-cyano-3-(1-benzyl-2-chloro-3-indolyl)acrylate or a pharmaceutically acceptable salt thereof.

7. A pharmaceutical composition comprising a compound according to claim 1 together with a pharmaceutically acceptable carrier or diluent.

8. A pharmaceutical composition according to claim 7 in the form of an oral dosage unit or parenteral dosage unit.

9. A pharmaceutical composition according to claim 8, wherein said dosage unit comprises from about 1 to about 100 mg of a compound.

10. A method of treating a disease in the central nervous system via the metabotropic glutamate receptor system comprising administering to a subject in need thereof an effective amount of a compound according to claim 1.

11. A method according to claim 10 wherein said disease is epilepsy, senile dementia, Parkinson's disease, Huntington's Chorea, pain or deficiencies of mental and motoric performance seen after conditions of brain ischemia.

* * * * *